United States Patent [19]

Yoneyama et al.

[11] Patent Number: 5,208,378
[45] Date of Patent: May 4, 1993

[54] PROCESS FOR PRODUCTION OF WATER-SOLUBLE CARBODIIMIDE

[75] Inventors: Takahiro Yoneyama, Matsudo; Masaki Odagiri, Ushiku; Makoto Imanari, Ami, all of Japan

[73] Assignee: Research Association for Utilization of Light Oil, Tokyo, Japan

[21] Appl. No.: 732,123

[22] Filed: Jul. 18, 1991

[30] Foreign Application Priority Data

Jul. 19, 1990 [JP] Japan .................................. 2-189414

[51] Int. Cl.$^5$ .......................................... C07C 267/00
[52] U.S. Cl. ............................................... 564/252
[58] Field of Search ............................. 564/252, 17, 30

[56] References Cited

U.S. PATENT DOCUMENTS

| | | | |
|---|---|---|---|
| 2,675,382 | 4/1954 | Melamed | 564/511 |
| 3,201,463 | 8/1965 | Ruby | 564/252 |
| 4,097,605 | 6/1978 | Fancher | 564/17 |
| 4,990,232 | 2/1991 | Alden | 564/252 |

OTHER PUBLICATIONS

Sheehan et al. "A Convenient Synthesis of Water-Soluble Carbodiimides" *The Journal of Organic Chemisty*, vol. 26, No. 7 (1961) pp. 2525–2528.

Hoare et al., The Journal of Biological Chemistry, vol. 242, No. 10 (1967) pp. 2447–2453.

Sheehan et al., The Journal of Organic Chemistry, vol. 21, No. 4 (1956) pp. 439–441.

*Primary Examiner*—Glennon H. Hollrah
*Assistant Examiner*—Peter G. O'Sullivan
*Attorney, Agent, or Firm*—Wenderoth, Lind & Ponack

[57] ABSTRACT

A process for the production of a water-soluble carbodiimide, which comprises
(1) allowing ethyl isothiocyanate to react with N,N-dimethyl-1,3-propanediamine in an aromatic hydrocarbon solvent (first reaction step),
(2) removing hydrogen sulfide from a thiourea derivative formed in the first reaction step upon adding a hydrogen sulfide removing agent without isolating the thiourea derivative (second reaction step), and
(3) recovering a water-soluble carbodiimide from the resulting reaction mixture.

10 Claims, No Drawings

PROCESS FOR PRODUCTION OF WATER-SOLUBLE CARBODIIMIDE

BACKGROUND OF THE INVENTION

This invention relates to an industrially excellent process for the production of a water-soluble carbodiimide using ethyl isothiocyanate and N,N-dimethyl-1,3-propanediamine as starting materials.

Carbodiimides are an industrially profitable reaction aid widely used in the overall organic synthesis because they advance an esterification reaction or an amidation reaction, as a dehydrocondensation agent, under quite mild conditions. Especially, water-soluble carbodiimides containing a hydrophilic group in the skeleton are superior to general-purpose carbodiimides because of the following advantages.

1. They can be used in the reaction in a water solvent (e.g., D. C. Hoare, et al., The Journal of Biological Chemistry, 242, 2447 (1967)).
2. When used in an organic solvent, they can easily be removed by washing with dilute acid or water since the reaction residue is water-soluble (e.g., J. C. Sheehan, et al., Journal of Organic Chemistry, 21, 439 (1956)).

They are widely utilized chiefly in the synthesis or modification of peptides and phosphoric acid esters.

An ordinary method for forming water-soluble carbodiimides includes the following two methods as described in J. C. Sheehan, et al., Journal of Organic Chemistry, 26, 2525 (1961).

Method 1

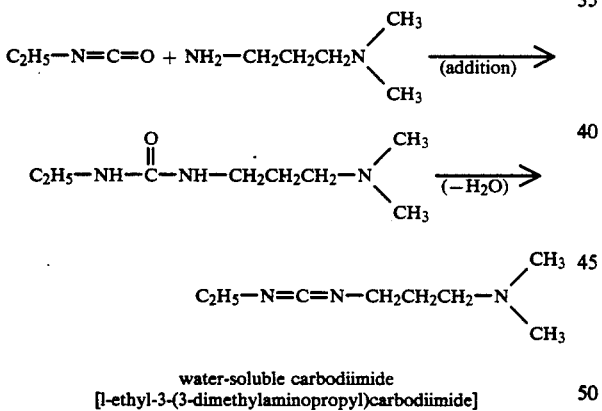

water-soluble carbodiimide
[1-ethyl-3-(3-dimethylaminopropyl)carbodiimide]

Method 2

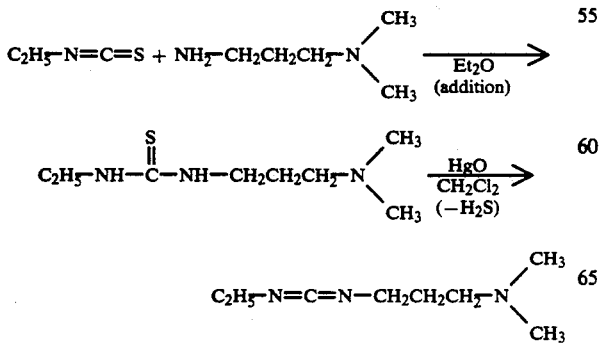

The above method 1, however, suffers the defects that the starting ethyl isocyanate is highly toxic and explosive and is even difficult to obtain beyond the problem of its handling. Meanwhile, the method 2 suffers the defects that an ether as a solvent is flammable and mercury oxide is toxic, as the fact that the well as operation is so complex and risky that a thiourea derivative as an intermediate must be once isolated and a solvent be exchanged. That is, there has been so far no industrially satisfactory process for producing water-soluble carbodiimides.

The first object of this invention is to provide a process for the production of a water-soluble carbodiimide using easy-to-handle, safe materials.

The second object of this invention is to provide a process for the production of a water-soluble carbodiimide which can eliminate the need of separation of the intermediate between the first and second reaction steps and can dispense with the exchange of the solvent.

The third object of this invention is to provide an industrial process for the production of a water-soluble carbodiimide which process is safe and simple in operation.

The other objects of this invention will be made clear from the foregoing explanation.

SUMMARY OF THE INVENTION

According to the investigations of the present inventors, the aforesaid objects and advantages of this invention can be achieved by a process for the production of a water-soluble carbodiimide, which comprises (1) allowing ethyl isothiocyanate to react with N,N-dimethyl-1,3-propanediamine in an aromatic hydrocarbon solvent (first reaction step), (2) removing hydrogen sulfide from a thiourea derivative formed in the first reaction step upon adding a hydrogen sulfide removing agent without isolating the thiourea derivative (second reaction step), and (3) recovering a water-soluble carbodiimide from the resulting reaction mixture.

DETAILED DESCRIPTION OF THE PREFERRED EMBODIMENTS OF THE INVENTION

This invention will be described in below.

In this invention, production of the water-soluble carbodiimide is basically carried out in accordance with the above Method 2. As shown by the following reaction scheme (I), isolation of the intermediate is not conducted nor needed, so that said production is excellent in the aspects of operation, safety and production cost.

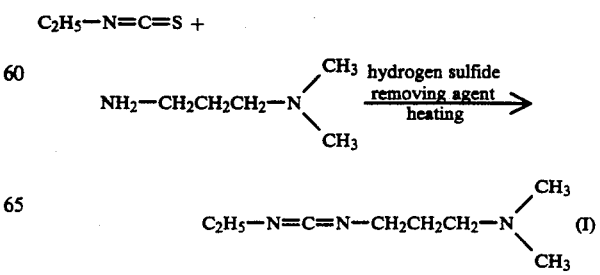

-continued water-soluble carbodiimide

The process of this invention is performed in the same aromatic hydrocarbon solvent in both the first and second reaction steps. The aromatic hydrocarbon solvent is preferably one having 6 to 10 carbon atoms. Especially preferable is benzene, toluene or a mixture thereof.

In the first reaction step of this invention, ethyl isothiocyanate is reacted with N,N-dimethyl-1,3-propanediamine in the aromatic hydrocarbon solvent to form chiefly a thiourea derivative. In this reaction, ethyl isothiocyanate and N,N-dimethyl-1,3-propanediamine are finally used at a molar ratio of 2:1 to 1:2, preferably 5:4 to 4:5.

A preferable method of the first reaction step will be described as follows. While the aforesaid amount of the solution of N,N-dimethyl-1,3-propanediamine (60 to 800 g/liter, preferably 100 to 500 g/liter) is added dropwise to the aromatic hydrocarbon solution of ethyl isothiocyanate (50 to 500 g/liter, preferably 100 to 300 g/liter), they are mixed with stirring. On this occasion, the reaction temperature is about −10 to about 80° C., preferably about 0 to about 50° C. The rate of dropwise addition is not particularly limited. As the reaction is an exothermic reaction, the rate of dropwise addition is properly adjusted to adapt to heat removability of the device to such an extent as to prevent abnormal increase of the temperature. When stirring is conducted at said temperature for 1 to 5 hours after the dropwise addition to completely effect the reaction, better results can be obtained.

In this invention, after the first reaction step is terminated as above, the second reaction step is successively carried out without isolating the formed thiourea derivative.

In the second reaction step, the reaction is run by adding the hydrogen sulfide removing agent to the reaction mixture containing the thiourea derivative formed in the first reaction step. At that time, the aforesaid solvent may be added to the reaction system. Examples of the hydrogen sulfide removing agent used in the second reaction step are lead oxides such as basic lead carbonate (2PbCo3.Pb(OH)2), litharge (PbO), red lead (Pb3O4) and lead dioxide (PbO2); and copper oxides such as cuprous oxide (Cu2O) and cupric oxide (CuO). Especially, basic lead carbonate, litharge and red lead are preferable because of the low cost.

The amount of the hydrogen sulfide removing agent used in the second reaction step is about 0.1 to about 10 mole, preferably 0.2 to 5 mole per mole of the thiourea derivative formed in the first reaction step. The heating temperature is about 30 to about 200° C., preferably about 50° C. to a boiling point of a solvent (e.g., about 80° C. in case of benzene and about 110° C. in case of toluene). The heating time is 0.1 to 10 hours, preferably 0.5 to 5 hours.

Because water is formed as a by-product in the reaction of the second reaction step, the water may be removed by adding a drying agent such as calcium chloride or magnesium sulfate to the reaction system, or by trapping azeotrope with the solvent as required. After the reaction, the intended water-soluble carbodiimide is isolated in a usual manner by filtration or decantation, and subsequently vacuum distillation after the removal of the solvent. If required, the product can be isolated by converting it into a salt such as a hydrochloric acid salt or a tetraalkyl ammonium salt. The procedures in the process of this invention can all be carried out at normal pressures except the distillation.

Compared to the conventional methods, the process for the production of the water-soluble carbodiimide in this invention alleviates toxicity and danger of the starting materials and conducts the two-step reaction in the same solvent, markedly simplifying the operation. Thus, this invention has the effects that the water-soluble carbodiimide is supplied at low cost and the range of the industrial utilization is all the more enlarged.

EXAMPLES

This invention is illustrated more specifically by the following Examples.

EXAMPLE 1

A three-necked flask was charged with 300 ml of a solution of 5.61 g (64.4 mmole) of ethyl isothiocyanate in 25 ml of toluene. N,N-dimethyl-1,3-propanediamine 6.58 g (64.4 mmole) dissolved in 25 ml of toluene was added dropwise over a period of 2 hours under ice cooling in a $N_2$ atmosphere, followed by stirring at room temperature for 2 hours. To the solution were added 90 ml of toluene and 57.4 g (83.7 mmole) of red lead ($Pb_3O_4$), and the mixture was refluxed for 3 hours. After the reaction was over, the solution was filtrated, and toluene was evaporated in vacuo from the filtrate. Water-soluble carbodiimide (6.4 g) was obtained by vacuum distillation. A boiling point was 70 to 83° C/5 mmHg and a yield was 64%.

Analysis of the resulting water-soluble carbodiimide by NMR revealed the following.

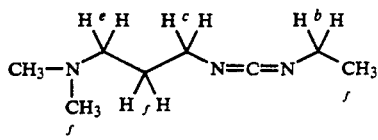

60MHz-$^1$H-NMR (TMS/CDCl$_3$) δppm:
1.23 (t,J=7.6 Hz,3H,a)
1 76 (tt,J=6.8 and 7.4 Hz,2H,d)
2.23 (s,6H,f)
2.34 (t,J=7.4 Hz,2H,e)
3.24 (q,J=7.2 Hz,2H,b)
3.27 (t,J=6.8 Hz,2H,c)

EXAMPLE 2

Example 1 was repeated except that the molar scale was 1/12 that of Example 1, and various metallic compounds including red lead and various heating conditions shown in Table 1 were used. Water-soluble carbodiimides were obtained in yields shown in Table 1.

TABLE 1

| Metallic compound | temperature (°C.) | time (hr) | yield (1) (%) |
|---|---|---|---|
| Pb3O4 | 80–90 | 10 | 40 |
| Pb3O4 | 80 (2) | 10 | 50 |
| 2PbCO3.Pb(OH)2 | 110 | 2 | 25 |
| PbO | " | " | 38 |
| PbO2 | " | " | 60 |
| Cu2O | " | " | 20 |
| CuO | " | " | 26 |

(1) by gas chromatography
In (2), refluxing in benzene was conducted, and in other cases, heating or refluxing in toluene was conducted.

What we claim is:

1. A process for the production of water-soluble carbodiimide, which comprises
   (1) allowing ethyl isothiocyanate to react with N,N-dimethyl-1,3-propanediamine in an aromatic hydrocarbon solvent selected from the group consisting of benzene, toluene and a mixture thereof (first reaction step),
   (2) removing hydrogen sulfide from a thiourea derivative formed in the first reaction step by adding a hydrogen sulfide removing agent selected from the group consisting of a lead oxide, a copper oxide and a mixture thereof and heating at a temperature of about 50° C. to a reflux temperature without isolating the thiourea derivative (second reaction step), and
   (3) recovering the water-soluble carbodiimide from the resulting reaction mixture.

2. The process of claim 1 wherein the reaction in the first reaction step is performed at a temperature of about 0° C. to about 50° C.

3. The process of claim 1 wherein the reaction in the first reaction step is performed by mixing a solution containing about 50 g/liter to about 500 g/liter of ethyl isothiocyanate with about 60 g/liter to about 800 g/liter of N,N-dimethyl-1,3-propanediamine.

4. The process of claim 1 wherein in the second reaction step, the hydrogen sulfide removing agent is added in an amount of about 0.1 to about 10 mols per mol of the thiourea derivative present in the reaction mixture of the first reaction step.

5. The process of claim 1 wherein in the first reaction step, the molar ratio of ethyl isothiocyanate:N,N-dimethyl-1,3-propanediamine is 2:1 to 1:2.

6. The process of claim 1 wherein the lead oxide is a member selected from the group consisting of a basic lead carbonate (2PbCO$_3$.Pb(OH)$_2$), a litharge (PbO), a red lead (Pb$_3$O$_4$) and a lead dioxide (PbO$_2$).

7. The process of claim 1 wherein the copper oxide is a member selected from the group consisting of cuprous oxide (Cu$_2$O) and cupric oxide (CuO).

8. The process of claim 1 wherein the lead oxide is a red lead (Pb$_3$O$_4$) or a lead dioxide (PbO$_2$).

9. The process of claim 1 wherein the reaction in the second reaction step is performed at a temperature of about 80° C. to 110° C.

10. A process for the production of a water-soluble carbodiimide, which comprises
    (1) allowing ethyl isothiocyanate to react with N,N-dimethyl-1,3-propanediamine in an aromatic hydrocarbon solvent selected from the group consisting of benzene, toluene and a mixture thereof (first reaction step),
    (2) removing hydrogen sulfide from a thiourea derivative formed in the first reaction step by adding a hydrogen sulfide removing agent selected from the group consisting of red lead (Pb$_3$O$_4$) and lead dioxide (PbO$_2$) and heating at a temperature of about 80° C. to 110° C. without isolating the thiourea derivative (second reaction step), and
    (3) recovering the water-soluble carbodiimide from the resulting reaction mixture.

* * * * *